United States Patent
Appavoo et al.

(10) Patent No.: US 9,994,691 B2
(45) Date of Patent: *Jun. 12, 2018

(54) ANTIMICROBIAL CLEANSING COMPOSITION

(71) Applicant: Conopco, Inc., d/b/a UNILEVER, Englewood Cliffs, NJ (US)

(72) Inventors: Shanthi Appavoo, Chennai (IN); Anindya Dasgupta, Bangalore (IN); Satyaranjan Gupta, Hadapsar Pune (IN); Divya Paruchuri, Hyderabad (IN); Maya Treesa Saji, Bangalore (IN); Neha Salgaonkar, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/513,998

(22) PCT Filed: Sep. 14, 2015

(86) PCT No.: PCT/EP2015/070953
§ 371 (c)(1),
(2) Date: Mar. 24, 2017

(87) PCT Pub. No.: WO2016/050493
PCT Pub. Date: Apr. 7, 2016

(65) Prior Publication Data
US 2017/0247523 A1  Aug. 31, 2017

(30) Foreign Application Priority Data
Sep. 29, 2014  (EP) ..................................... 14186861

(51) Int. Cl.
| | | |
|---|---|---|
| *C11D 9/10* | (2006.01) |
| *C08K 3/08* | (2006.01) |
| *C11D 9/26* | (2006.01) |
| *A61Q 19/10* | (2006.01) |
| *C11D 9/06* | (2006.01) |

(52) U.S. Cl.
CPC ................ *C08K 3/08* (2013.01); *A61Q 19/10* (2013.01); *C11D 9/06* (2013.01); *C11D 9/10* (2013.01); *C11D 9/26* (2013.01); *C11D 9/267* (2013.01); *A61K 2800/5426* (2013.01); *C08K 2003/0806* (2013.01)

(58) Field of Classification Search
None
See application file for complete search history.

(56) References Cited

U.S. PATENT DOCUMENTS

| 2,864,769 A | 12/1958 | Lutz et al. |
| 2010/0098776 A1 | 4/2010 | Carnali et al. |
| 2011/0224120 A1 | 9/2011 | Meine et al. |

FOREIGN PATENT DOCUMENTS

| CA | 586350 | 11/1959 |
| GB | 759950 | 10/1956 |
| WO | WO2011131422 | 10/2011 |

OTHER PUBLICATIONS

IPRP in PCTEP2015070953, dated Sep. 6, 2016.
Search Report in EP14186861, dated Mar. 4, 2015.
Search Report in PCTEP2015070953, dated Nov. 24, 2015.
Written Opinion in EP14186861, dated Mar. 4, 2015.
Written Opinion in PCTEP2015070953, dated Nov. 24, 2015.

*Primary Examiner* — Necholus Ogden, Jr.
(74) *Attorney, Agent, or Firm* — Ronald A. Koatz

(57) ABSTRACT

The present invention relates to an antimicrobial cleansing composition and a method of cleaning or disinfecting a surface. The invention more particularly relates to an antimicrobial cleansing composition that provides antimicrobial efficacy in cleaning applications having relatively short contact times. An object of the present invention is to provide an antimicrobial cleansing composition that exhibits biocidal activity in relatively short contact times of 1 minute to 10 seconds. Another object of the present invention is to provide an antimicrobial cleansing composition which exhibits antimicrobial activity at very low concentration of silver compound. A further object of the present invention is to provide an antimicrobial cleansing composition which has consumer-acceptable aesthetic properties. A still further object of the present invention is to provide an antimicrobial composition that is highly efficacious against a broad spectrum of gram positive and gram negative bacteria. We have determined that antibacterial activity in relatively short contact times against gram positive and gram negative microorganisms in a soap based cleansing composition having silver compound enhances considerably in presence of a further salt of carboxylic acid. It has been additionally found that the antibacterial activity is enhanced even at very low concentrations of silver compound.

12 Claims, No Drawings

ANTIMICROBIAL CLEANSING COMPOSITION

FIELD OF THE INVENTION

The present invention relates to an antimicrobial cleansing composition and a method of cleaning or disinfecting a surface. The invention more particularly relates to an antimicrobial cleansing composition that provides antimicrobial efficacy in cleaning applications having relatively short contact times.

BACKGROUND OF THE INVENTION

Soap based cleansing composition provides antibacterial benefits largely associated with the removal of organisms from a surface through the cleansing/detergency action of such products. Such compositions commonly have biocidal action against many gram negative bacteria. The biocidal action of soap compositions against gram positive bacteria is considerably more limited within the contact times typical of product use, generally under 1 minute, and more commonly of the order of 30 seconds or less. Achieving biocidal action against gram positive bacteria is especially problematic in the case of high pH cleansing compositions, by which is meant that a 1 wt % solution thereof in water has a pH in a range of from 9 to 12 at 25° C.

Various routes to improving the biocidal activity of soap based cleansing compositions have been suggested.

US2008014247A (Lu et al., 2008) discloses a composition having metal containing material, stearic acid and a pharmaceutically acceptable carrier to treat conditions caused by gram-positive, gram-negative, fungal pathogens and/or antibiotic-resistant bacteria. It further provides a method for inhibiting biofilm proliferation. The metal containing material can be silver.

U.S. Pat. No. 3,050,467 B1 (Horowitz et al. 1962) discloses an antimicrobial cleansing composition consisting essentially of a mixture of a water-soluble soap and a silver salt of partially depolymerized alginic acid. The composition provides synergestic antimicrobial activity.

US2011224120 AA (Henkel) discloses liquid washing compositions having surfactant, silver and/or a silver compound and a non-neutralized fatty acid.

Our copending application EP14152965 (Unilever, 2014) discloses an alkaline cleansing composition of pH at least 9 having anionic surfactant including soap, silver and 0.01 to 10 wt % fatty acids providing a robust cleaning composition.

When silver compound is used in soap based cleaning compositions, silver at levels providing antimicrobial benefits as suggested in prior art is relatively unstable, undergoes discoloration and is aesthetically unpleasant.

Prior disclosures have not addressed the issue of providing an antimicrobial cleansing composition that affords an effective, fast, and broad spectrum control of bacteria and exhibits acceptable aesthetic properties.

Thus an object of the present invention is to provide an antimicrobial cleansing composition that provides biocidal activity in relatively short contact times of 1 minute to 10 seconds.

Another object of the present invention is to provide an antimicrobial cleansing composition which provides antimicrobial activity at very low concentration of silver compound.

A further object of the present invention is to provide an antimicrobial cleansing composition which has consumer-acceptable aesthetic properties.

A still further object of the present invention is to provide an antimicrobial composition that is highly efficacious against a broad spectrum of gram positive and gram negative bacteria.

We have determined that antibacterial activity in relatively short contact times against gram positive and gram negative microorganisms in a soap based cleansing composition having silver compound enhances considerably in presence of a further salt of carboxylic acid. It has been additionally found that the antibacterial activity is enhanced even at very low concentrations of silver compound.

Given the relatively high cost of silver, such low levels of silver compound provides for significant cost benefits, compared to the higher levels of silver compounds required to provide significant biocidal effect within the contact times of interest. Additionally, the low levels of silver compound are desirable from both a sensory and process vantage.

SUMMARY OF THE INVENTION

According to a first aspect of the present invention disclosed is an antimicrobial cleansing composition comprising:
(i) 1 to 85 wt % of a fatty acid soap;
(ii) 0.1 to 100 ppm of a silver(I) compound; and further comprises,
(iii) 0.1 to 10 wt % of a salt of carboxylic acid.

According to a second aspect of the present invention disclosed is a method of cleaning or disinfecting a surface comprising the steps of applying a composition of the first aspect on to said surface and at least partially removing the composition from the surface.

The invention will now be explained in detail.

DETAILED DESCRIPTION OF THE INVENTION

Except in the operating and comparative examples, or where otherwise explicitly indicated, all numbers in this description indicating amounts, parts, percentages, ratios, and proportions of material, physical properties of material, and conditions of reaction are to be understood as modified by the word "about". All parts, percentages, ratios, and proportions of material referred to in this description are by weight unless otherwise indicated.

The term "comprising" is meant not to be limiting to any subsequently stated elements but rather to encompass non-specified elements of major or minor functional importance. In other words, the listed steps, elements or options need not be exhaustive. Whenever the words "including" or "having" are used, these terms are meant to be equivalent to "comprising" as defined above. Where the compositions of the subject invention are described as "including" or "comprising" specific components or materials, narrower embodiments where the compositions can "consist essentially of" or "consist of" the recited components or materials are also contemplated.

It should also be noted that in specifying any range of concentration or amount, any particular upper concentration or amount can be associated with any particular lower concentration or amount.

The compositions of the present invention are preferred for medical or non-medical use, and more particularly preferred for cosmetic use in removing plaque on the surfaces of the oral cavity.

Antimicrobial Cleansing Composition

Disclosed antimicrobial cleansing composition includes a fatty acid soap, a silver (I) compound and further includes a salt of carboxylic acid.

Fatty Acid Soap:

Disclosed antimicrobial cleansing composition includes a fatty acid soap. The term "fatty acid soap" or, more simply, "soap" is used here in its popular sense, i.e., salts of aliphatic alkane- or alkene monocarboxylic fatty acids preferably having 6 to 22 carbon atoms, and more preferably 8 to 18 carbon atoms.

Usually a blend of fatty acids is used to get a blend of fatty acid soaps. The term "soap" refers to sodium, potassium, magnesium, mono-, di- and tri-ethanol ammonium cation or combinations thereof. In general, sodium soaps are preferred in the compositions of this invention, but up to 15% or even more of the soap content may be some other soap forms such as potassium, magnesium or triethanolamine soaps.

Preferably the fatty acid blend is made from fatty acids that may be different fatty acids, typically fatty acids containing fatty acid moieties with chain lengths of from $C_8$ to $C_{22}$. The fatty acid blend may also contain relatively pure amounts of one or more fatty acids. Suitable fatty acids include, but are not limited to, butyric, caproic, caprylic, capric, lauric, myristic, myristelaidic, pentadecanoic, palmitic, palmitoleic, margaric, heptadecenoic, stearic, oleic, linoleic, linolenic, arachidic, gadoleic, behenic and lignoceric acids and their isomers.

The fatty acid blend preferably includes relatively high amounts (e.g., at least 3%, preferably at least 10%) of capric and lauric acids. Further preferably the fatty acid blend includes low levels of myristic acid, (e.g. preferably less than 4% by wt.) which generally provides good lathering property.

In preferred embodiments, the fatty acid blend has proportion of capric acid to lauric acid ranging from 0.5 to 1 to 1.5 to 1.

Soaps having the fatty acid distribution of coconut oil and palm kernel oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available triglyceride fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85 percent fatty acids having about 12 to 18 carbon atoms. The preferred soaps for use in the present invention should include at least about 30 percent saturated soaps, i.e., soaps derived from saturated fatty acids, preferably at least about 40 percent, more preferably about 50 percent, saturated soaps by weight of the fatty acid soap. Soaps can be classified into three broad categories which differ in the chain length of the hydrocarbon chain, i.e., the chain length of the fatty acid, and whether the fatty acid is saturated or unsaturated. For purposes of the present invention these classifications are: "Laurics" soaps which encompass soaps which are derived predominantly from C12 to C14 saturated fatty acid, i.e. lauric and myristic acid, but can contain minor amounts of soaps derived from shorter chain fatty acids, e.g., C10. Laurics soaps are generally derived in practice from the hydrolysis of nut oils such as coconut oil and palm kernel oil.

"Stearics" soaps which encompass soaps which are derived predominantly from C16 to C18 saturated fatty acid, i.e. palmitic and stearic acid but can contain minor level of saturated soaps derived from longer chain fatty acids, e.g., C20. Stearic soaps are generally derived in practice from triglyceride oils such as tallow, palm oil and palm stearin.

Oleic soaps which encompass soaps derived from unsaturated fatty acids including predominantly oleic acid, linoleic acid, myristoleic acid and palmitoleic acid as well as minor amounts of longer and shorter chain unsaturated and polyunsaturated fatty acids. Oleics soaps are generally derived in practice from the hydrolysis of various triglyceride oils and fats such as tallow, palm oil, sunflower seed oil and soybean oil. Coconut oil employed for the soap may be substituted in whole or in part by other "high-laurics" or "laurics rich" oils, that is, oils or fats wherein at least 45 percent of the total fatty acids are composed of lauric acid, myristic acid and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

Disclosed composition includes 1 to 85 wt % of a fatty acid soap. Preferably the fatty acid soap is present in an amount not more than 80 wt %, more preferably not more than 75 wt %, still more preferably not more than 65 wt %, further preferably not more than 55 wt % and still further preferably not more than 45 wt % and most preferably not more than 35 wt % but preferably not less than 5 wt %, more preferably not less than 10 wt %, still more preferably not less than 15 wt % and further preferably not less than 20 wt % and most preferably not less than 25 wt %.

Silver(I) Compound:

Disclosed antimicrobial cleansing composition includes 0.1 to 100 ppm silver (I) compound. Preferably the silver compounds are water-soluble having a silver ion solubility at least $1.0 \times 10^{-4}$ mol/L (in water at 25° C.). Silver ion solubility, as referred to herein, is a value derived from a solubility product (Ksp) in water at 25° C., a well known parameter that is reported in numerous sources. More particularly, silver ion solubility [Ag+], a value given in mol/L may be calculated using the formula:

$$[Ag+]=(Ksp \cdot x)^{(1/(x+1))}$$

wherein Ksp is the solubility product of the compound of interest in water at 25° C., and x represents the number of moles of silver ion per mole of compound. It has been found that Silver(I) compounds having a silver ion solubility of at least $1 \times 10^{-4}$ mol/L in are suitable for use herein. Silver ion solubility values for a variety of silver compounds are given in Table 1:

TABLE 1

| Silver Compound | X | Ksp (mol/L in water at 25° C.) | Silver Ion Solubility [Ag+] (mol/L in water at 25° C.). |
|---|---|---|---|
| silver nitrate | 1 | 51.6 | 7.2 |
| Silver acetate | 1 | $2.0 \times 10^{-3}$ | $4.5 \times 10^{-2}$ |
| Silver sulfate | 2 | $1.4 \times 10^{-5}$ | $3.0 \times 10^{-2}$ |
| Silver benzoate | 1 | $2.5 \times 10^{-5}$ | $5.0 \times 10^{-3}$ |
| Silver salicylate | 1 | $1.5 \times 10^{-5}$ | $3.9 \times 10^{-3}$ |
| Silver carbonate | 2 | $8.5 \times 10^{-12}$ | $2.6 \times 10^{-4}$ |

TABLE 1-continued

| Silver Compound | X | Ksp (mol/L in water at 25° C.) | Silver Ion Solubility [Ag+] (mol/L in water at 25° C.). |
|---|---|---|---|
| Silver citrate | 3 | $2.5 \times 10^{-16}$ | $1.7 \times 10^{-4}$ |
| Silver oxide | 1 | $2.1 \times 10^{-8}$ | $1.4 \times 10^{-4}$ |
| Silver phosphate | 3 | $8.9 \times 10^{-17}$ | $1.3 \times 10^{-4}$ |
| Silver chloride | 1 | $1.8 \times 10^{-10}$ | $1.3 \times 10^{-5}$ |
| Silver bromide | 1 | $5.3 \times 10^{-13}$ | $7.3 \times 10^{-7}$ |
| Silver iodide | 1 | $8.3 \times 10^{-17}$ | $9.1 \times 10^{-9}$ |
| Silver sulfide | 2 | $8.0 \times 10^{-51}$ | $2.5 \times 10^{-17}$ |

A preferred silver(I) compound is selected from silver oxide, silver nitrate, silver acetate, silver sulfate, silver benzoate, silver salicylate, silver carbonate, silver citrate and silver phosphate, more preferably the silver compound is silver oxide, silver sulfate or silver citrate and still further preferred silver(I) compound is silver oxide or silver sulphate.

Preferably in the disclosed antimicrobial cleansing composition silver (I) compound is present at levels not less than 0.4 ppm, still preferably not less than 0.5 ppm and further preferably not less than 1 ppm and it is preferred that the silver (I) compound in the composition is present at levels not more than 80 ppm, more preferably not more than 50 ppm, further preferably not more than 20 ppm and still further preferably not more than 10 ppm and most preferably not more than 5 ppm. It is highly preferred that the silver (I) compound in the antimicrobial cleansing composition is present at 0.5 to 5 ppm.

Salt of Carboxylic Acid:

Disclosed antimicrobial cleansing composition further includes 0.1 to 10% by weight of a salt of carboxylic acid.

The composition preferably has not less than 0.5% by weight, more preferably not less than 0.75% by weight and still more preferably not less than 1% by weight of the salt of carboxylic acid. The composition preferably has not more than 5% by weight, more preferably not more than 3% by weight and still more preferably not more than 1.25% by weight of the salt of carboxylic acid.

Disclosed salt of carboxylic acid is preferably a salt of mono, di or tri carboxylic acid. When the salt of carboxylic acid is a salt of mono-carboxylic acid, the mono-carboxylic acid preferably has 1 to 6 carbon atoms more preferably the mono-carboxylic acid is selected from lactate or benzoate. More preferably the salt of carboxylic acid is a salt of di or tri carboxylic acid. When the salt of carboxylic acid is a salt of a di-carboxylic acid it preferably has 1 to 12 carbon atoms and when the salt of carboxylic acid is a salt of tri-carboxylic acid it preferably has 1 to 18 carbon atoms. It is further preferred that the salt of di or tri carboxylic acid is chosen from an oxalic, fumaric, phthalic, maleic, malic, malonic or citric acid. The di or tricarboxylic acid is most preferably a malic, malonic, or citric acid. It is possible that the part of the di or tri-carboxylic acid that is added to prepare the composition of the invention is present as salt of the di or tricarboxylic acid depending on the pH at which the composition is formulated. In such cases, the salt is preferably alkali metal or alkaline earth metal salts, more preferably alkali metal salts of which sodium salt is most preferred. Structure of salts of some of the carboxylic acids is given below:

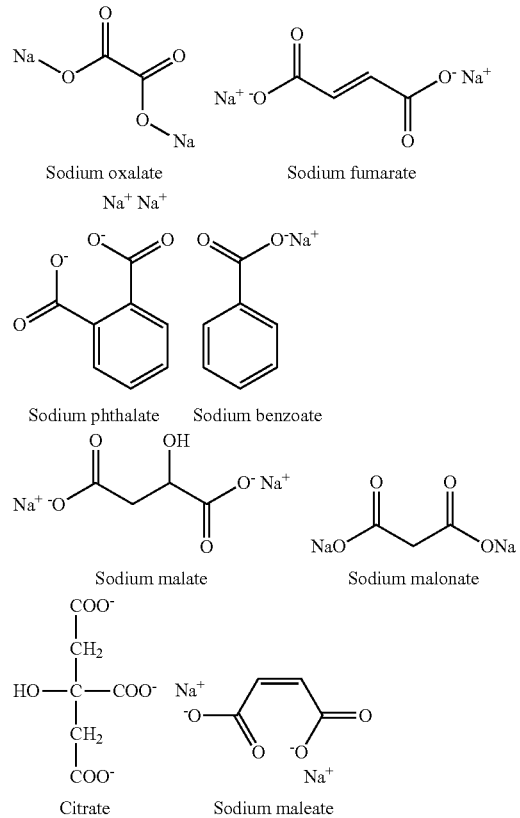

Salt of carboxylic acid in the disclosed composition is preferably selected from oxalate, lactate, fumarate, phthalate, benzoate, maleate, malate, malonate or citrate more preferably the salt of carboxylic acid is selected from a lactate, malate, malonate, or citrate.

It is observed that inclusion of a salt of di or tri carboxylic acid in the composition of the invention provides for the desired antimicrobial efficacy while the efficacy of mono carboxylic acids is comparatively less.

The non-metal salts of carboxylic acid are also preferably be used in the present invention. The most preferred non-metal salt of carboxylic acid is ammonium benzoate.

Preferably, the salt of carboxylic acid used in the invention may be a mixture of two or more salts of carboxylic acid. The mixture may also preferably between metal and non-metal salt of carboxylic acid.

Optional Ingredients:

Surfactant

If desired, the formulations may optionally include a detersive surfactant in addition to the fatty acid soap. Such detersive surfactants include, for example, anionic, zwitterionic and/or nonionic surfactants.

Examples of anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof.

The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative zwitterionic surfactants are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

Nonionic surfactants which may be used include the reaction products of compounds having a hydrophobic group and a reactive hydrogen atom. Exemplative are alcohols, acids, amides or alkyl phenols reacted with alkylene oxides, especially ethylene oxide either alone or with propylene oxide. Specific nonionics are $C_6$-$C_{22}$ alkyl phenolsethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides. Also useful are the alkyl polysaccharides.

Preferred surfactant is an anionic surfactant or amphoteric surfactant. Anionic surfactant is preferably an alkyl ether sulphate.

Form of the Composition

The composition preferably may be in the form of a solid, soft solid, gel, emulsion, or liquid.

Preferably a 1 wt % solution of the composition in water has a pH in a range of from 9 to 12 at 25° C.

When the disclosed composition is in the solid form, the composition is preferably a bar. The soap bar may be prepared by the milled and plodded route or may be prepared using the melt cast route. Of the two routes the milled and plodded route is more preferred for preparing a soap bar of the present invention.

Personal wash compositions are available in various forms such as soap bars, transparent soap bars including cast-bars, liquid soaps including liquid hand wash compositions, creams and gel based products. Commercial soap compositions have one or more "soaps", which has the meaning as normally understood in the art; salts of mono carboxylic fatty acids. The counterions of the salts are generally sodium, potassium, ammonium or alkanoammonium ions, but other suitable ions known in the art may also be used. Compositions based on soaps, i.e. soap bars generally contain anywhere from 15 to 80% by weight alkali metal salt of fatty acids, depending on whether the soap is in solid or liquid form, which accounts for the total fatty matter (TFM), the remainder being water (about 10-20%) and other ingredients such as metal ion chelators, color, perfume, preservatives etc. Structurants and fillers are also frequently added to such compositions in small amount to replace some of the soap, while retaining the desired properties of the product. Soaps having TFM content of about 70 are called "toilet soaps", whereas those having TFM of about 40 are called "bathing bars". In a soap bar, the composition preferably comprises 0.1 to 5% hydrotrope.

Method of Cleaning and Disinfecting a Surface

According to a second aspect of the present invention there is provided a method of cleaning or disinfecting a surface comprising the steps of applying a composition of the first aspect onto said surface and at least partially removing the composition from the surface.

Preferably the method of at least partially removing the composition is carried out less than 5 minutes after the step of applying the composition on the substrate.

The composition is preferably diluted with water in a weight ratio of 1:10 to 1:40, preferably in a ratio of 1:20 to 1:30, before or during the step of applying the composition on the surface.

The method preferably comprises a step of rinsing the surface with a suitable solvent preferably water or the surface may be wiped with a suitable wipe.

The inventors have determined that the composition of the invention provides an antimicrobial action where the contact time of the antimicrobial actives with the surface is low, i.e. of the order of less than 5 minutes, preferably less than 2 minutes, further more preferably less than a minute and in many cases less than 15 seconds.

The invention will now be demonstrated by way of the following non-limiting examples.

EXAMPLES

The following protocol was used to evaluate biocidal activity.

In-Vitro Time-Kill Protocol

Fatty acid soap composition: A composition as shown on Table 2 was prepared.

Stock of a salt of carboxylic acid: A 20% stock of a salt of carboxylic acid was separately prepared. 20% stock solutions of each of sodium citrate, sodium malonate, sodium lactate and sodium benzoate were prepared.

Stock of silver compound: A 0.01 mg/mL stock of silver compound was prepared. The stock was thoroughly vortexed before adding it into the fatty acid soap composition.

TABLE 2

| Fatty acid soap composition | Wt % |
| --- | --- |
| Potassium salt of fatty acid (lauric acid, myristic acid, palmitic acid) | 14.6 |
| Butylated Hydroxytoluene (BHT) | 0.05 |
| Ethylenediaminetetraacetic acid (EDTA) | 0.13 |
| Cellulose Ether (Methocel ™ 40-100 from Dow Chemical) | 0.5 |
| Glycerin | 0.5 |
| Potassium Hydroxide | 3.5 |
| Ethyl glycol distearate (EGDS) | 1 |
| Potassium Chloride | 3 |
| Demineraised water and other minors | to make it to 100 |

Preparation of Comparative and Preferred Composition

Comparative composition 1 (Comp 1): 5 grams of soap composition provided on Table 2 was diluted in 4 mL of sterile distilled water at room temperature.

Comparative composition 2 (Comp 2): To 5 grams of soap composition provided on Table 2, 0.5 mL of 20% stock solution of sodium citrate was added and mixed thoroughly. The resultant mixture was diluted with 3.5 mL of sterile distilled water at room temperature.

Comparative composition 3 (Comp 3): To 5 grams of soap composition provided on Table 2, 1 mL of 0.01 mg/mL of stock solution of $Ag_2O$ was added and mixed thoroughly. The resultant mixture was diluted with 3 mL of sterile distilled water at room temperature.

Comparative composition 4 (Comp 4): To 5 grams of soap composition provided on Table 2, 1 mL of 0.01 mg/mL of stock solution of $Ag_2SO_4$ was added and mixed thoroughly. The resultant mixture was diluted with 3 mL of sterile distilled water at room temperature.

Preferred Example 1 (Ex 1): To 5 grams of soap composition provided on Table 2, 1 mL of 0.01 mg/mL of stock solution of $Ag_2O$ and 0.5 mL of 20% stock solution of sodium citrate were added and mixed thoroughly and then diluted with 2.5 mL of sterile distilled water at room temperature.

Preferred Example 2 (Ex 2): To 5 grams of soap composition provided on Table 2, 1 mL of 0.01 mg/mL of stock solution of $Ag_2SO_4$ and 0.5 mL of 20% stock solution of sodium citrate were added and mixed thoroughly and then diluted with 3 mL of sterile distilled water at room temperature.

Preferred Example 3 (Ex 3): To 5 grams of soap composition provided on Table 2, 1 mL of 0.01 mg/mL of stock solution of $Ag_2O$ and 0.5 mL of 20% stock solution of sodium malonate were added and mixed thoroughly and then diluted with 3 mL of sterile distilled water at room temperature.

Preferred Example 4 (Ex 4): To 5 grams of soap composition provided on Table 2, 1 mL of 0.01 mg/mL of stock solution of $Ag_2O$ and 0.5 mL of 20% stock solution of sodium lactate were added and mixed thoroughly and then diluted with 3 mL of sterile distilled water at room temperature.

Preferred Example 5 (Ex 5): To 5 grams of soap composition provided on Table 2, 1 mL of 0.01 mg/mL of stock solution of $Ag_2SO_4$ and 0.5 mL of 20% stock solution of sodium benzoate were added and mixed thoroughly and then diluted with 3 mL of sterile distilled water at room temperature. The comparative composition and the preferred composition are shown in Table 3.

Preparation of the Bacterial Culture

*Escherichia.coli* ATCC 10536 was used in the study to represent gram negative bacteria and *Staphylococcus aureus* ATCC 6538 was used to represent gram positive bacteria. The bacteria were grown overnight on Trypticase soya agar (TSA) plate. The bacterial cell density was then adjusted at 620 nm to a pre-calibrated optical density to get the final count of $10^8$ cfu/ml in saline (0.8% NaCl) by using a spectrophotometer.

Assay Protocol 9 mL of the comparative composition 1 (Comp 1) was taken in a sample container to which 1 mL of bacterial culture was added just before performing the assay and mixed well to obtain a mixture. The mixture was kept for a specific contact time of either 10 seconds, 30 seconds, 1 minute or 5 minutes.

At the end of the contact time the antibacterial activity of the comparative composition 1 (Comp1) was neutralized immediately, by addition of 1 mL of the above mixture to 9 mL of D/E broth (39 gpl-Difco). The neutralized samples were then serially diluted upto 5 dilution in D/E broth and plated on TSA (40 gpl-Difco) in duplicates.

The above mentioned assay protocol was similarly followed for all other comparative and preferred compositions.

For the assay, the control used was a mixture prepared by addition of 1 mL of bacterial culture to 9 mL of saline; the mixture was then serially diluted and plated on TSA. After solidification of the TSA plates, the plates were incubated at 37° C. for 48 hours. The colonies on the plates were counted. The log reduction was calculated by comparing with the control.

TABLE 3

Biocidal activity
$Log_{10}$ Reduction against *S. aureus* ATCC 6538

| | | Contact time | |
|---|---|---|---|
| Example | Composition | 10 seconds | 30 seconds |
| Comp 1 | Fatty acid soap | 0.4 | 0.6 |
| Comp 2 | Fatty acid soap + 1 wt % sodium citrate | 0.6 | 0.8 |
| Comp 3 | Fatty acid soap + 1 ppm $Ag_2O$ | 1.1 | 2.8 |
| Ex 1 | Fatty acid soap + 1 ppm $Ag_2O$ + 1 wt % sodium citrate | 2.3 | >5 |
| Comp 4 | Fatty acid soap + 1 ppm $Ag_2SO_4$ | 1.0 | 3.0 |
| Ex 2 | Fatty acid soap + 1 ppm $Ag_2SO_4$ + 1 wt % sodium citrate | 1.7 | >5 |

The data in Table 3 demonstrates that, at the indicated contact times, the preferred compositions Ex1 and Ex 2 had greater bactericidal efficacy against *S. aureus* ATCC 6538 than the comparative composition (Comp1, Comp 2, Comp 3 and Comp 4).

TABLE 4

Biocidal activity
$Log_{10}$ Reduction against *E. coli* ATCC 10536

| Example | Composition | Contact time 10 seconds |
|---|---|---|
| Comp 1 | Fatty acid soap | 2.6 |
| Comp 2 | Fatty acid soap + 1 wt % sodium citrate | 3.5 |
| Comp 3 | Fatty acid soap + 1 ppm $Ag_2O$ | 3.3 |
| Ex 1 | Fatty acid soap + 1 ppm $Ag_2O$ + 1 wt % sodium citrate | >5 |
| Ex 3 | Fatty acid soap + 1 ppm $Ag_2O$ + 1 wt % sodium malonate | >5 |
| Ex 4 | Fatty acid soap + 1 ppm $Ag_2O$ + 1 wt % sodium lactate | >5 |
| Ex 5 | Fatty acid soap + 1 ppm $Ag_2SO_4$ + 1 wt % sodium benzoate | >5 |

The data in Table 4 demonstrates that, at the indicated contact times, that the preferred compositions Ex 1, 3, 4 and 5 had greater bactericidal efficacy against *E. coli* ATCC 10536 than the comparative composition (Comp1, Comp 2, Comp 3). The data on Table 4 also indicates that improved bacterial efficacy against *E. coli* ATCC 10536 is shown by various salts of carboxylic acid for example malonate, lactate, benzoate and citrate in cleansing compositions having fatty acid soap and silver (I) compound.

In another set of experiments non-metal salts of carboxylic acid and a mixture of a metal and a non-metal salt of carboxylic acid has been used:

The fatty acid soap composition for these sets of experiments has been given below in Table 5.

TABLE 5

| Fatty acid soap composition | Wt % |
|---|---|
| Lauric Acid | 5.8 |
| Myristic Acid | 6.7 |
| Palmitic Acid | 2.1 |
| Butylated Hydroxytoluene (BHT) | 0.05 |
| Ethylenediaminetetraacetic acid (EDTA) | 0.13 |
| Methocel 40-100 (The Dow Chemical Company) | 0.5 |
| Glycerin | 0.5 |
| Potassium Hydroxide | 3.5 |
| SLES, 1EO (70%) | 3 |
| Cocamidopropyl betaine (CAPB) | 2.5 |
| Ethyl glycol distearate (EGDS) | 1 |
| Potassium Chloride | 3 |
| Demineraised water | To 100 |

Preparation of Comparative and Preferred Composition

Comparative composition 5 (Comp 5): 5 grams of soap composition of Table 5 with 1 ppm of $Ag_2O$ (as silver DTPA complex) was diluted with 5 mL of sterile distilled water at room temperature.

Preferred Example 6 (Ex 6): 5 grams of soap composition of Table 5 with 1 ppm of $Ag_2O$ (as silver DTPA complex) and 4% of ammonium benzoate was diluted with 5 mL of sterile distilled water at room temperature.

Preferred Example 7 (Ex 7): 5 grams of soap composition of Table 5 with 1 ppm of $Ag_2O$ (as silver DTPA complex), 2% of ammonium benzoate and 2% ammonium citrate was diluted with 5 mL of sterile distilled water at room temperature.

Preferred Example 8 (Ex 8): 5 grams of soap composition of Table 5 with 1 ppm of $Ag_2O$ (as silver DTPA complex), 2% of ammonium benzoate and 2% sodium citrate was diluted with 5 mL of sterile distilled water at room temperature.

The silver DTPA complex as mentioned above was prepared by using 1.500 g of Silver oxide powder with 22.5 g of 40% Na5DTPA (Sodium salt of diethylene triamine pentaacetic acid). The above mixture was stirred and heated at ~45° C. in a water bath for 10 minutes. Any particulates observed are broken with glass rod. After that 975 g of water was added water stirring ambient temp (~25° C.). The stirring was continued for 10 minutes. After that 0.8 g of powdered lauric acid was added and stirred for 30 minutes. The resulting mixture was centrifuged to separate out the supernatant from the residue for 5 minutes. The supernatant is silver DTPA complex used in the experiments.

The assay protocol is same as described in the previous section.

TABLE 6

Biocidal activity
$Log_{10}$ Reduction against *S. aureus* ATCC 6538

| Example | Composition | Contact time (10 seconds) |
|---|---|---|
| Comp 5 | Fatty acid Soap + 1 ppm $Ag_2O$ (as Silver DTPA complex) | 1.7 |
| Ex 6 | Fatty acid Soap + 1 ppm $Ag_2O$ (as Silver DTPA complex) + 4% Ammonium Benzoate | 2.4 |
| Ex 7 | Fatty acid Soap + 1 ppm $Ag_2O$ (as Silver DTPA complex) + 2% Ammonium Benzoate + 2% Ammonium citrate | 3.2 |
| EX 8 | Fatty acid Soap + 1 ppm $Ag_2O$ (as Silver DTPA complex) + 2% Ammonium Benzoate + 2% sodium citrate | 3.4 |

The data in Table 6 demonstrates that, at the indicated contact time of 10 seconds, the preferred compositions Ex 6, Ex 7 and Ex 8 had greater bactericidal efficacy against *S. aureus* ATCC 6538 than the comparative composition (Comp 5).

The invention claimed is:

1. An antimicrobial cleansing composition comprising:
   (i) 1 to 85% by weight of a fatty acid soap;
   (ii) 0.1 to 100 ppm by weight of a silver(I) compound; and, further comprises,
   (iii) 0.5 to 10% by weight of a salt of carboxylic acid wherein the salt of carboxylic acid is a non-metal salt of carboxylic acid.

2. A composition as claimed in claim 1 wherein the fatty acid soap comprises an alkali metal salt of aliphatic alkane- and/or alkene monocarboxylic acids having 8 to 18 carbon atoms.

3. A composition as claimed in claim 1 wherein said composition further comprises a surfactant selected from anionic surfactant or amphoteric surfactant.

4. A composition as claimed in claim 3 wherein said anionic surfactant is alkyl ether sulphate.

5. A composition as claimed in claim 1 wherein at 25° C., a 1 wt % solution of the composition in water has a pH in a range of from 9 to 12.

6. A composition as claimed in claim 1 wherein the salt of carboxylic acid is selected from an oxalate, lactate, fumarate, phthalate, benzoate, maleate, malate, malonate or citrate.

7. A composition as claimed in claim 6 wherein said salt of carboxylic acid is selected from a lactate, malate, malonate, or citrate.

8. A composition as claimed in claim 1 wherein said silver compound (I) is a silver oxide or silver sulphate.

9. A composition as claimed in claim 1 comprising 0.5 to 5 ppm silver (I) compound.

10. A composition as claimed in claim 1 is in the form of a bar, liquid or gel.

11. A method of cleaning or disinfecting a surface comprising the steps of applying a composition as claimed in claim 1 on to said surface and at least partially removing the composition from the surface.

12. A method as claimed in claim 11 wherein the step of at least partially removing the composition is carried out less than 5 minutes after the step of applying the composition on the substrate.

* * * * *